US00PP23828P3

(12) United States Plant Patent
Jensen

(10) Patent No.: US PP23,828 P3
(45) Date of Patent: Aug. 13, 2013

(54) ASTER PLANT NAMED 'DASGRA'

(50) Latin Name: *Symphyotrichum novi-belgii*
Varietal Denomination: DASGRA

(75) Inventor: Bent Juhl Jensen, Malling (DK)

(73) Assignee: Gartneriet Raahoj, Malling (DK)

( * ) Notice: Subject to any disclaimer, the term of this patent is extended or adjusted under 35 U.S.C. 154(b) by 0 days.

(21) Appl. No.: 13/137,759

(22) Filed: Sep. 12, 2011

(65) Prior Publication Data

US 2012/0180174 P1 Jul. 12, 2012

(30) Foreign Application Priority Data

Feb. 15, 2011 (QZ) ..... PBR 201/0084

(51) Int. Cl.
*A01H 5/00* (2006.01)

(52) U.S. Cl.
USPC ..... Plt./355

(58) Field of Classification Search
USPC ..... Plt./355
See application file for complete search history.

(56) References Cited

PUBLICATIONS

Trademark Electronic Service System (TESS) retrieved on Nov. 7, 2012, citation for 'Mystery Lady', 2 pages.*
UPOV. PLUTO: PLant Variety Database, retrieved Oct. 22, 2012, citation for QZ PBR 20110084, 'Dasgra', 3 pages.*

* cited by examiner

*Primary Examiner* — Howard Locker
(74) *Attorney, Agent, or Firm* — Foley & Lardner LLP

(57) ABSTRACT

A new and distinct cultivar of Aster plant named 'DASGRA', characterized by its upright and somewhat outwardly spreading plant habit, dark green foliage, freely flowering habit, decorative-type inflorescences with dark violet ray florets, and few disk florets (i.e., "double" capitulae.)

3 Drawing Sheets

Latin name of genus and species of the plant claimed: *Symphyotrichum novi-belgii.*
Variety denomination: 'DASGRA'.

BACKGROUND OF THE INVENTION

The present invention relates to a new and distinct cultivar of Aster plant, botanically known as *Symphyotrichum novi-belgii*, and hereinafter referred to by the name 'DASGRA'.

The new Aster is a product of a planned breeding program conducted by the Inventor in Malling, Denmark. The objective of the breeding program is to create new potted Aster cultivars with uniform plant growth habit, desirable floret colors, and good postproduction longevity.

The new Aster originated from a cross-pollination made by the Inventor in Malling, Denmark in September 2009, between the Aster cultivar named 'MYSTERY LADY MARLENE' (U.S. Plant patent application Ser. No. 13/064,118 (now abandoned). as pollen parent, and the Aster cultivar named 'RH 06-515-005' (unpatented) as seed parent. The new Aster was discovered and selected by the Inventor as a single flowering plant within the progeny of the stated cross-pollination grown in a controlled environment in Malling, Denmark. The selection of this plant was based on its uniform plant growth habit and desirable inflorescence form and ray floret color.

Asexual reproduction of the new Aster by vegetative tip cuttings was first conducted in Malling, Denmark during June, 2010. Asexual reproduction by cuttings has shown that the unique features of this new Aster are stable and reproduced true to type in successive generations.

SUMMARY OF THE INVENTION

The cultivar 'DASGRA' has not been observed under all possible environmental conditions. The phenotype may vary somewhat with variations in environment such as temperature, day-length, and/or light level, without, however, any variance in genotype.

The following traits have been repeatedly observed and are determined to be the unique characteristics of 'DASGRA'. These characteristics in combination distinguish 'DASGRA' as a new and distinct Aster cultivar:

1. Upright and somewhat outwardly spreading plant habit;
2. Dark green foliage;
3. Freely flowering habit;
4. Decorative-type inflorescences with dark violet colored ray florets; and
5. Few disk florets (i.e., "double" capitulae).

Plants of the instant cultivar 'DASGRA' differ primarily from plants of the seed parent, the unpatented cultivar named 'RH 06-515-005', in the following characteristics:

1. plants of 'DASGRA' are more compact than plants of 'RH 06-515-005';
2. plants of the 'DASGRA' have more ray florets per inflorescence than plants of the cultivar 'RH 06-515-005'; and
3. plants of the 'DASGRA' have different ray floret coloration than plants of the cultivar 'RH 06-515-005'.

Plants of the instant cultivar 'DASGRA' differ primarily from plants of the pollen parent, the cultivar named 'MYSTERY LADY MARLENE', in the following characteristics:

1. plants of 'MYSTERY LADY MARLENE' are more compact than plants of 'DASGRA';
2. plants of 'MYSTERY LADY MARLENE' have differently shaped leaves than plants of 'DASGRA'; and
3. plants of 'MYSTERY LADY MARLENE' have different ray floret coloration than plants of the cultivar 'DASGRA'.

Plants of the instant cultivar 'DASGRA' also differ from plants of the cultivar 'MYSTERY LADY CELINE' (CPVO Application No. 2007/2428) in that plants of 'DASGRA' have dark violet ray florets, while 'MYSTERY LADY CELINE' has purple-violet ray florets.

Plants of the instant cultivar 'DASGRA' also differ from plants of the cultivar 'VICTORIA FANNY' (Patented, U.S. Plant Pat. No. 13,360) in the following characteristics:

1. plants of 'DASGRA' have more ray florets per inflorescence (about 250) than plants of 'VICTORIA FANNY' (about 150); and
2. plants of 'DASGRA' have dark violet colored ray florets (RHS 83B), while plants of 'VICTORIA FANNY' have violet ray florets (RHS 88B to 88C).

Plants of the instant cultivar 'DASGRA' also differ from plants of the cultivar 'MYSTERY LADY DEBBIE' (unpatented) in the following characteristics:

1. plants of 'DASGRA' have spatulate, twisted ray florest while plants of 'MYSTERY LADY DEBBIE' have flat, lanceolate ray florets; and
2. plants of 'DASGRA' have a predominant dark violet color (RHS 83B) while plants of 'MYSTERY LADY DEBBIE' have a predominant violet-blue color (RHS 90A).

BRIEF DESCRIPTION OF THE PHOTOGRAPHS

The accompanying colored photographs illustrate the overall appearance of the new Aster 'DASGRA', showing the colors as true as it is reasonably possible to obtain in colored reproductions of this type. Colors in the photographs may differ slightly from the color values cited in the detailed botanical description, which more accurately describe the actual colors of 'DASGRA'.

DETAILED BOTANICAL DESCRIPTION

Figure 1:
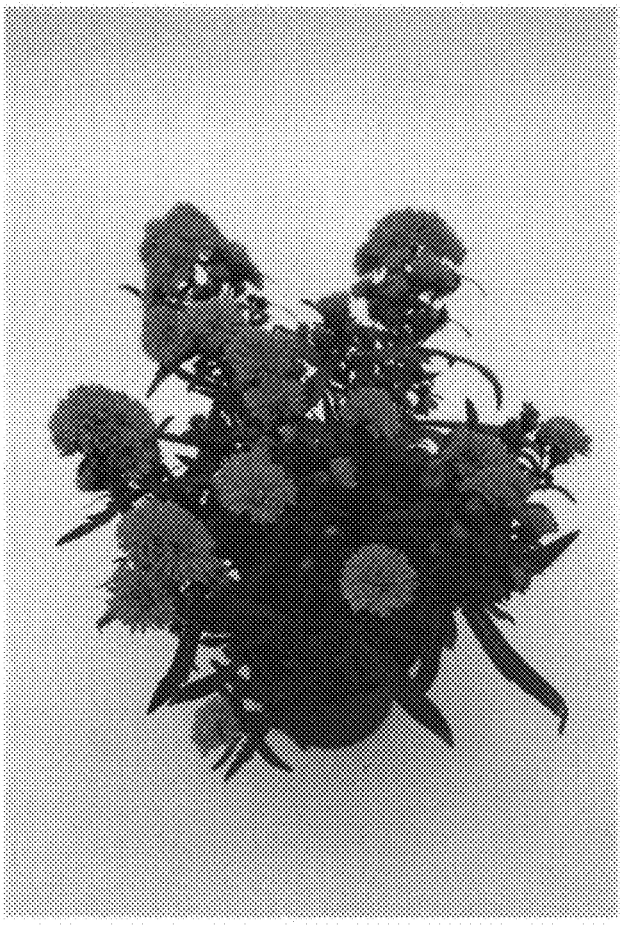
FIG. 1 shows a side-top down perspective view of a typical flowering plant of 'DASGRA'.
Figure 2:
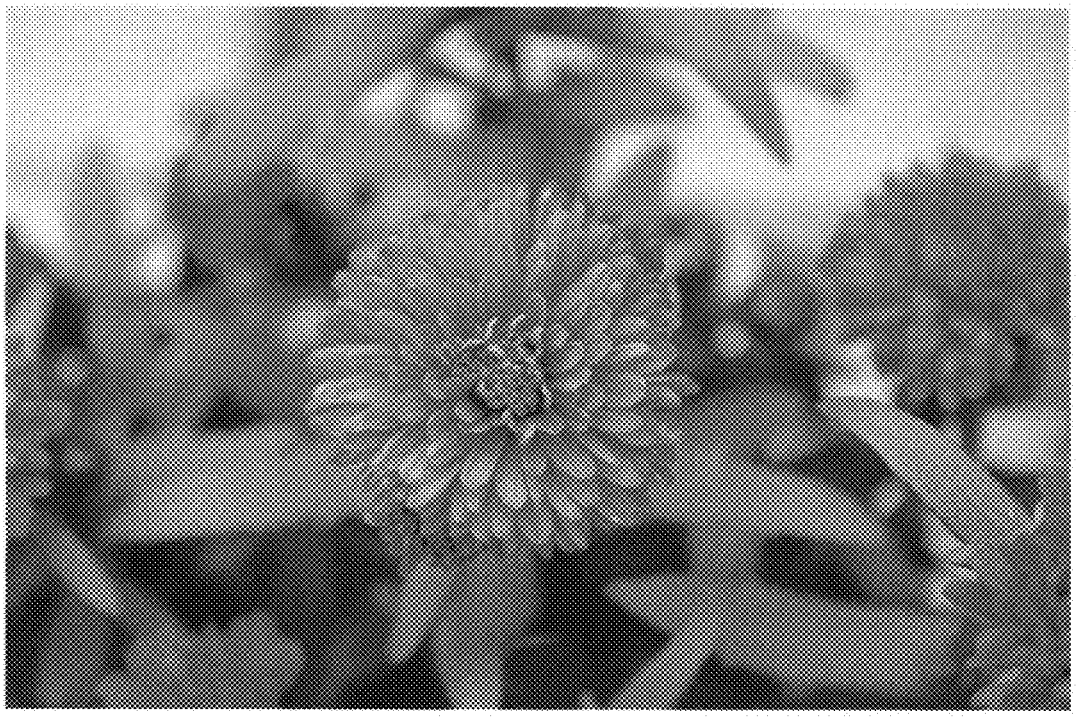
FIG. 2 shows a close-up view of typical flowers (capitulae) of 'DASGRA'.
Figure 3:
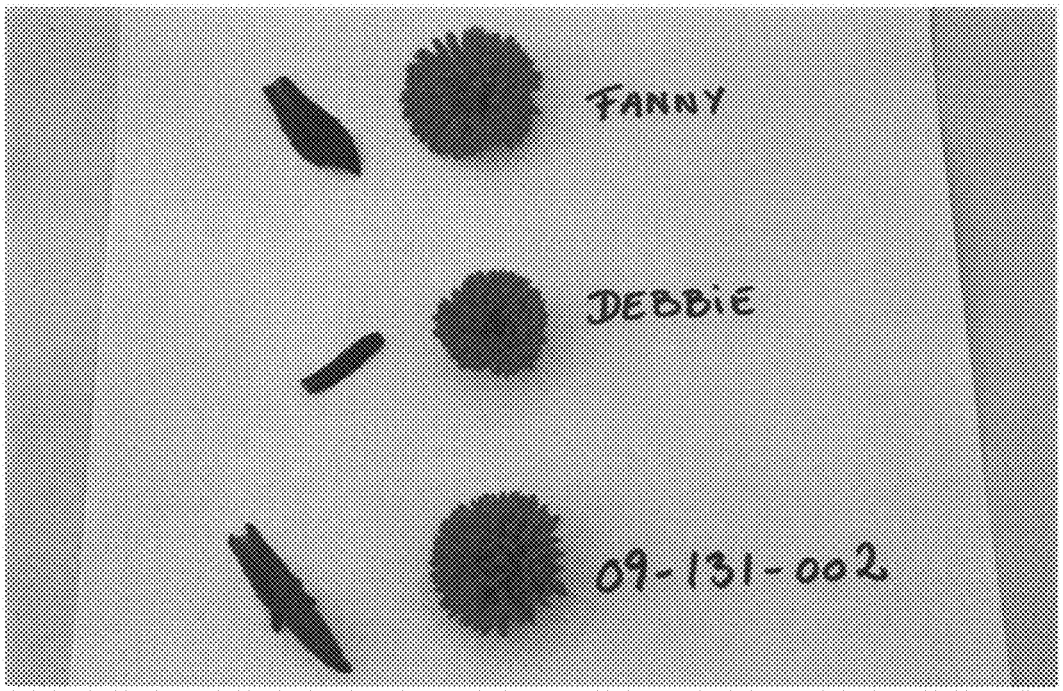
FIG. 3 shows a close up view of the upper surfaces of typical inflorescences and leaves of 'DASGRA' (coded 09-131-002) as compared to 'MYSTERY LADY DEBBIE' and 'VICTORIA FANNY'.

In the following description, color references are made to The Royal Horticultural Society Colour Chart, 4$^{th}$ Edition, except where general terms of ordinary dictionary significance are used. The aforementioned photographs, following observations and measurements describe plants grown and flowered during the autumn in Malling, Denmark, in a glass-covered greenhouse and under conditions which approximate those generally used in commercial potted Aster production. During the production of these plants, day and night temperatures were about 18 to 20 degree C.

3 cuttings were planted in 9.5 cm pots and pinched twice and treated three times with growth retardant daminozide. Data for a description of the claimed variety when not treated with growth retardant is not available. Plants were about 10 weeks old when the photographs and the botanical description were taken.

Classification:

*Botanical.*—*Symphyotrichum novi-belgii.*

Parentage:

*Female* (*seed*) *parent*.—Aster cultivar named 'RH 06-515-005' (Breeder Reference, unpatented).

*Male* (*pollen*) *parent*.—Aster cultivar named 'MYSTERY LADY MARLENE' (U.S. Plant patent application Ser. No. 13/064,118 (now abandoned)).

Propagation:

*Type cutting*.—Terminal vegetative cuttings.

*Time to initiate roots*.—Summer: About 12 days at 21° C. Winter: About 13 days at 21° C.

*Root habit*.—Freely branching.

*Root color*.—White, close to RHS 155D.

*Root texture*.—Fine, fibrous.

Plant description:

*Form*.—Herbaceous, decorative-type potted plant, with stems upright and somewhat outwardly spreading, inverted conical plant habit, appropriate for 9-15 cm containers.

*Plant height* (*from pot rim to top of plant plane*).—About 14-17 cm.

*Plant spread* (*width*).—About 25 cm.

*Lateral branches*.—Length: About 6-8 cm. Diameter: About 3 mm. Strength: Strong. Angle: Mostly erect. Texture: Glaucescent. Color: RHS 137C, green.

Foliage description:

*Leaves*.—Arrangement: Alternate, subulate, decurrent. Overall shape: Lanceolate. Apex shape: Acute. Base shape: Decurrent, auriculate, ½ clasping. Length: Up to 7 cm. Width: Up to 15 mm. Margin: Dentate with 4-6 points per leaf. Texture (both sides): Glabrous, smooth, leathery. Foliage Color: Mature: Upper surface: Green, RHS 139A. Under Surface: Gray-green, RHS 189A. Immature: Upper surface: Green, RHS 139A. Under Surface: Gray-green, RHS 189A. Venation: Color: Upper surface: Green, RHS 139A-C. Under surface: Yellow-green, RHS 146B. Roots: Texture: fine, fibrous. Color: Gray-white, RHS 156D.

Inflorescence description:

*Inflorescence arrangement and shape*.—Upright decorative-type capitulate inflorescences in racemes; spatulate, twisted ray florets and some tubular disk florets; terminate and few axillary inflorescences; disk and ray florets develop acropetally on a capitulum. Persistent.

*Natural flowering season*.—Late summer. 5 weeks of long day treatments (20 hours) induces budding.

*Flower longevity*.—Inflorescences maintain good color and substance for about five weeks in an interior environment, longer if temperatures are kept below 20 degree C.

*Inflorescence size*.—Height: About 1.5 cm. Diameter: About 3.5 cm.

*Number of inflorescences per plant*.—About 50.

*Buds*.—Length: About 6 mm. Diameter: About 7 mm. Shape: Globular. Color: Yellow-green, RHS147B.

*Peduncles*.—Length: 1 cm. Diameter: 3 mm. Color: Green, RHS 137A.

*Ray florets*.—Arrangement: In about12 whorls. Quantity per inflorescence: About 250-300. Length: About 11 mm. Width: About 3 mm. Overall Shape: Linear, twisted. Apex: Rounded. Base: Attenuate. Margin: Entire. Texture: Smooth, glabrous. Orientation: Initially upright, later more horizontal. Aspect: Twisted to slightly involute. Color when opening: Upper surface: Dark Violet, RHS 83B; Under surface: Dark Violet, RHS 83B. Color when opened: Upper surface: Dark Violet, RHS 83B. Under surface: Dark Violet, RHS 83B. Disc Florets: Number and Arrangement:

30 per capitulum; 5 base petals fused to form a tube. Texture: parchment-like. Length: 1 mm. Color: Base: Light green, RHS 142D. Middle: White, RHS 155A. Tip: Violet, RHS 84A.

*Involucres—Phyllaries*.—Quantity per inflorescence: About 40 to 50. Length: About 5 mm. Width: Less than 3 mm. Shape: Lanceolate. Apex: Acute. Base: Truncate, fused. Texture, upper and lower surfaces: Setulose edges, verrucose abaxial. Color: Upper and under surfaces: RHS 137A-D.

Reproductive organs:

*Androecium*.—Present only in disk florets. Stamen: Quantity: 5, fused. Length: 4 mm. Color: Grayed-yellow, RHS 162B. Pollen: Present.

*Gynoecium*.—Present only in disk florets (ray florets are sterile). Quantity per floret: 1. Stigma: Shape: Bifurcate. Color: White, RHS 155D.

Fragrance: No characteristic fragrance.

Seed/fruit: None observed.

Weather tolerance: No specific testing or observation for frost tolerance. Generally hardy to −15° C. if acclimatized.

Disease/pest resistance: None observed.

Disease/pest susceptibility: None observed.

What is claimed is:

1. A new and distinct cultivar of Aster plant designated 'DASGRA', as illustrated and described herein.

* * * * *